United States Patent
Qu et al.

(10) Patent No.: US 11,535,884 B2
(45) Date of Patent: Dec. 27, 2022

(54) METHODS AND KITS FOR TARGETED ENRICHMENT OF TARGET DNA WITH HIGH GC CONTENT

(71) Applicant: BERRY GENOMICS CO., LTD, Beijing (CN)

(72) Inventors: Ziwei Qu, Beijing (CN); Tao Yu, Beijing (CN); Fangming Wang, Beijing (CN); Nannan Zhang, Beijing (CN); Jianguang Zhang, Biejing (CN)

(73) Assignee: BERRY GENOMICS CO., LTD., Beijing (CN)

(*) Notice: Subject to any disclaimer, the term of this patent is extended or adjusted under 35 U.S.C. 154(b) by 76 days.

(21) Appl. No.: 16/761,458

(22) PCT Filed: Feb. 7, 2018

(86) PCT No.: PCT/CN2018/075543
§ 371 (c)(1),
(2) Date: May 4, 2020

(87) PCT Pub. No.: WO2019/085320
PCT Pub. Date: May 9, 2019

(65) Prior Publication Data
US 2020/0263235 A1     Aug. 20, 2020

(30) Foreign Application Priority Data
Nov. 3, 2017 (CN) .......................... 201711070776.0

(51) Int. Cl.
*C12Q 1/6806* (2018.01)
*C12Q 1/6869* (2018.01)

(52) U.S. Cl.
CPC ......... *C12Q 1/6806* (2013.01); *C12Q 1/6869* (2013.01); *C12Q 2537/159* (2013.01); *C12Q 2565/519* (2013.01)

(58) Field of Classification Search
CPC .................. C12Q 2531/119; C12Q 1/6869
See application file for complete search history.

(56) References Cited

U.S. PATENT DOCUMENTS

2020/0362403 A1* 11/2020 Serantes .............. C12Q 1/6855

FOREIGN PATENT DOCUMENTS

| CN | 102203273 A | 9/2011 |
|----|-------------|--------|
| CN | 105190656 A | 12/2015 |
| CN | 105803055 A | 7/2016 |
| CN | 107236729 A | 10/2017 |
| WO | 2008/097887 A2 | 8/2008 |
| WO | 2010/127020 A1 | 11/2010 |
| WO | 2014/113204 | 7/2014 |
| WO | 2016/028887 A1 | 2/2016 |

OTHER PUBLICATIONS

Extended European Search Report dated Jul. 9, 2021 issued in European Application No. 18874699.4.
International Search Report dated Aug. 23, 2018 issued in International Application (No. PCT/CN2018/075543).
Written Opinion dated Aug. 23, 2018 issued in International Application (No. PCT/CN2018/075543).

\* cited by examiner

*Primary Examiner* — Teresa E Strzelecka
(74) *Attorney, Agent, or Firm* — Womble Bond Dickinson (US) LLP; Cristin Howley Cowles

(57) ABSTRACT

The present invention relates to a method for enrichment of target DNA with high GC content based on target sequence capture and multiple displacement amplification, as well as a kit suitable for this method. The present invention also relates to a method for constructing a sequencing library of target DNA with high GC content based on the enrichment method of the present invention.

14 Claims, 3 Drawing Sheets

METHODS AND KITS FOR TARGETED ENRICHMENT OF TARGET DNA WITH HIGH GC CONTENT

TECHNICAL FIELD

The present application relates to a method for enrichment of target DNA with high GC content, which is particularly suitable for constructing a long-read sequencing library of sequences with high GC content. The present application also relates to a kit used in the said method.

BACKGROUND

Regions rich in GC within the genome are often closely related to the regulation of gene expression, the changes of chromosome structure, genetic diseases and the like[1]. As the hairpin-shaped secondary structure formed between the G-C bases by complementary match within the DNA regions of high GC content is relatively stable, it is always difficult and being a technical challenge for the accurate sequencing of DNA regions having high GC content (i.e., GC content generally is equal to or greater than 80%).

Currently, detection methods such as Sanger sequencing and capillary electrophoresis are used in the detection of DNA with high GC content, and these methods are essentially established on the basis of polymerase chain reactions (PCR). However, it is difficult for PCR to effectively amplify DNA regions with high GC content, especially those completely comprised of C/G bases[4]. Although essential efforts have been made to modify the DNA polymerase, to optimize the design of primers, to optimize the temperature conditions for PCR reactions, to use PCR accelerators such as dimethyl sulfoxide, betaine and the like which are capable of reducing DNA secondary structures, and have improved the amplification efficiency of DNA regions having high GC content to a certain degree[5-8], the results are not very consistent, as the amplification efficiency is often depends on the complexity of the sequence and composition of the DNA template molecules. In addition, even if small amount of DNA products having high GC content are obtained by PCR amplification and detected by high-resolution capillary electrophoresis, such detection can only detects the size and abundance of the products, but not the base sequence of the DNA. On the other hand, Sanger sequencing and the second generation high throughput sequencing can read the DNA sequences, but these methods are also based on PCR amplification, thus are not efficient and accurate for sequencing of DNA with high GC content.

Altogether, there are two main technical issues in the detection of high GC content DNA sequences: (1) targeted library construction or enrichment of target regions with high GC content; and (2) sequencing of target regions with high GC content. Previously, Loomis et al. have performed sequencing on a target DNA sequence comprising up to 750 CGG repeat units using single molecule real-time sequencing (SMRT)[9]. This can be attributed to the advantages of the recently developed third generation high throughput sequencing methods represented by single molecule real-time sequencing and nanopore sequencing. These sequencing methods are not only able to read longer reads, but also can sequence a single molecule directly without a PCR step in the sequencing process, thereby avoiding the PCR-induced limitation on the sequencing against high GC content regions, and really achieving the integrity of sequencing coverage[10]. However, the target DNA with a high GC content used in the sequencing method of Loomis et al. is obtained by plasmid cloning and PCR amplification[9]. It is known that plasmid cloning is time consuming and laborious, while PCR amplification still has the problem of low amplification efficiency and amplification error tendencies. Further, Pham et al. have reported recently a third generation method for sequencing target DNA having a high GC content without amplification and enrichment. Specifically, the genome DNA is treated by a type IIS restriction enzyme followed by connection with hairpin-shaped linkers comprising specific sequences, and treatment with an exonuclease. Then, molecules comprising complete DNA-linkers conjunction are maintained and subjected to a targeted sequencing using SMRT hook primers having specific sequences[11]. However, the method disclosed by Pham et al. also has some obvious problems. For example, the fragment digested by the restriction enzyme used in said method generally has a length of several hundreds of bases, which may impose some difficulties on the continuous sequencing of target DNA fragment with a bigger size (for example, greater than 1 kb). Moreover, this method is conducted without a step of enrichment or amplification of the template DNA, thus it requires a relatively large amount of initial DNA.

Given that the third generation sequencing platforms can perform sequencing on high GC content DNA easily and accurately[10], the main problem needs to be addressed currently is the targeted enrichment of high GC content DNA efficiently and accurately, which satisfies the requirements of the sequencing platforms. The targeted enrichment first requires separation of target regions. Currently, the well-established target sequence capture technology can specifically separate the target sequences by hybridizing the genome DNA with specific probes, which are designed and synthesized according to the sequence of the target regions in the genome.

The product captured by probe hybridization is single-stranded DNA, which will be converted into double-stranded DNA for amplification and enrichment, and then for library construction and sequencing. The multiple displacement amplification (MDA) utilizes DNA polymerase with strand displacement activity to achieve high-efficient amplification of super-long template DNA under constant temperature[13]. More importantly, MDA can also achieve accurate, high-efficient amplification of high GC content regions (see FIG. 1), thereby obtaining efficient enrichment of target DNA with high GC content as well as double-stranded DNA. Accordingly, the present invention combines the specific feature of the target sequence capture technology in directional separation of the target area and the advantages of MDA in efficient amplification of high GC regions, and provides a method and kit for target enrichment of DNA with high GC content based on the technologies such as target sequence capture and multiple displacement amplification.

The present invention further provides, based on the above method for target enrichment, a method for constructing a library suitable for long reads sequencing platform, which includes but not limited to single molecule real-time sequencing (SMRT) and nanopore sequencing.

DESCRIPTION

The present invention aims at solving the existing problem that sequences with high GC content are difficult to be amplified efficiently by PCR, thus are difficult to be sequenced accurately. Thus, the present invention relates to a method and kit for target enrichment of DNA fragments with high GC content based on the target sequence capture and multiple displacement amplification technologies. Target regions with high GC content can be efficiently enriched using the method and kit of the present invention, while avoiding the problem of low efficiency or even failure of amplification as well as non-specific amplification occurred during PCR amplification in classic enrichment method. By this way, DNA fragments with a length equal to or larger than 2 kb can be obtained, which is suitable for further long reads high throughput sequencing.

Thus, in a first aspect, the present invention provides a method for enrichment of target DNA with high GC content, comprising the following steps:

(a) designing single-stranded oligonucleotide probes against specific flanking sequences of the target DNA with high GC content, and capturing the target DNA from the genome by target sequence capture technology;

(b) amplifying the captured target DNA with high GC content using multiple displacement amplification so as to obtain amplification product;

(c) subjecting the amplification product to enzyme digestion to remove branched DNA intermediate, so as to obtain digested product;

(d) purifying DNA fragment with a length equal to or larger than 2 kb, so as to obtain enriched target DNA with high GC content.

In one embodiment, the GC content of the target DNA with high GC content is between 80% and 100%.

In one embodiment, the captured target DNA has a length of 2 kb to 30 kb.

In one embodiment, said target sequence capture technology is hybridization between the single-stranded oligonucleotide probes and the genome DNA.

In one embodiment, methods for designing single-stranded oligonucleotide probes (also referred as "capture probes") are known to one skilled in the art, for example, different companies such as IDT, Nimblegen, Agilent, Illumina design said probes based on the properties of their own products. Although probes from different companies may vary in terms of modification, length or position distribution, they are designed based on the principle of base pairing with the complementary target sequences. Given that regions with high GC content are highly redundant within the genome, to capture the target region more specifically, the present invention specifically requires the capture probes to be designed and synthesized against the specific flanking sequences of the target DNA with high GC content, but not against the target DNA per se.

As used herein, the term "flanking sequences" refers to nucleotide sequences flanking the target DNA with high GC content, and its distance from the target DNA enables successful capture of the target DNA after hybridization. The term "specific flanking sequences" means that said flanking sequences is specific to the target DNA with high GC content, which specificity enables the binding of the single-stranded oligonucleotide capture probes designed against it to said flanking sequences, but not to other nucleotide sequences, thereby capturing the target DNA between the flanking sequences.

In one embodiment, the capture probes carry a label for modification, such as a biotin label, a fluorescence label and the like. Preferably, the label is a biotin label. The methods for hybridizing capture probes with target DNAs are known to one skilled in the art, wherein the hybridization conditions such as hybridization temperature, hybridization time as well as concentrations of various agents can be determined and adjusted by conventional techniques.

In one embodiment, DNA polymerase used in MDA is a polymerase for isothermal amplification with displacement activity. Preferably, said DNA polymerase is phi29.

In one embodiment, primers used in MDA are primers modified with 3'-thiophosphate bonds. In one preferable embodiment, said primers are 6-10 nucleotides in length, preferably 6-7 nucleotides in length. For example, primers can be 5'-NpNpNpNpNpSNpSN-3', wherein N denotes dA, dT, dC or dG, p denotes the phosphodiester bond, and pS denotes the thiophosphate bond. Said primers can be designed according to any known methods in the art. Further, reaction conditions for MDA, such as duration, temperature and the like are also known to one skilled in the art.

As used herein, the term "branched DNA intermediate" refers to DNA with branched structures presented in the MDA products, and its structure is not standard double-helix. As the structure of the branched DNA intermediate does not satisfy the requirement for the third generation sequencing, it should be removed by enzyme digestion during library construction. In one embodiment, the branched DNA intermediate is removed by nuclease, wherein said nuclease is preferably T7 Endonuclease I.

In one embodiment, after removal of the branched DNA intermediate from the MDA products, it is necessary to maintain long DNA fragments for use in the third generation sequencing, thus DNA fragments with a length equal to or greater than 2 kb is purified. Any method for purification known in the art can be applied to the present application, including but not limited to recovery by gel electrophoresis, column purification, and sorting by magnetic beads.

In a second aspect, the present invention provides a kit for enrichment of target DNA with high GC content, comprising reagents for capturing target DNA with high GC content, reagents for multiple displacement amplification, reagents for removing branched DNA intermediates, and reagents for purifying DNA fragments.

In one embodiment, the reagents for capturing target DNA with high GC content refers to any reagent suitable for capturing target DNA with high GC content from genome by hybridization, including but not limited to, capture probes, hybridization buffer, hybridization reagent, purification reagent and the like. Among such, the capture probes are designed against the specific flanking sequences of the target DNA with high GC content. Further, the capture probes can include a label such as a biotin label.

In one embodiment, the reagents for multiple displacement amplification include but not limited to polymerase for isothermal amplification, amplification buffer and the like. Preferably, the polymerase for isothermal amplification is phi29.

In one embodiment, the reagents for removing branched DNA intermediates include nuclease. Preferably, said nuclease is T7 Endonuclease I.

In one embodiment, the reagents for purifying DNA fragments refer to any reagent known in the art that can be used to purify DNA fragments having a length equal to or greater than 2 kb. Such reagents include but not limited to reagents used in gel electrophoresis recovery, column purification, and sorting by magnetic beads.

In a third aspect, the present invention provides a method for constructing a sequencing library of target DNA with high GC content, comprising mainly the following steps:

(1) enriching target DNA with high GC content using the method of the present invention;

(2) ligating enriched target DNA with high GC content to sequencing linkers, so as to obtain the sequencing library.

In one embodiment, said sequencing linkers are those matched with the sequencing platforms, and can be selected by one skilled in the art according to conventional techniques.

The sequencing library constructed according to the above method is particularly suitable for long reads high-throughput sequencing platforms, such as RSII and Sequel® sequencing platforms from Pacific Biosciences, as well as MinION® sequencing platforms from Oxford Nanopore, etc.

The methods and kits according to the present invention enable enrichment of target DNA having high GC content with high specificity, accurately and completely, as well as sequencing based on the third generation high-throughput sequencing platforms. The excellent technical effects of the methods and kits according to the present invention can be contributed to the following features.

(1) The capture probes are designed only against the specific sequences flanking the target DNA with high GC content, which successfully avoids the problem of difficulty in probe design and off-target effects resulted from high redundancy of regions having high GC content in the genome. This feature greatly increases the specificity of the enrichment of target DNA with high GC content.

(2) The captured products are enriched by multiple displacement amplification, which not only avoids the big hindrance occurred during the PCR step with respect to effective amplification of high GC regions, but also provides sufficient amount of long target double-stranded DNA having high GC content with accuracy and high efficiency. This feature makes the present invention particularly suitable for the third generation sequencing, thereby ensuring high accuracy of the sequencing results of the target DNA with high GC content.

FIGURES

Figure 4:
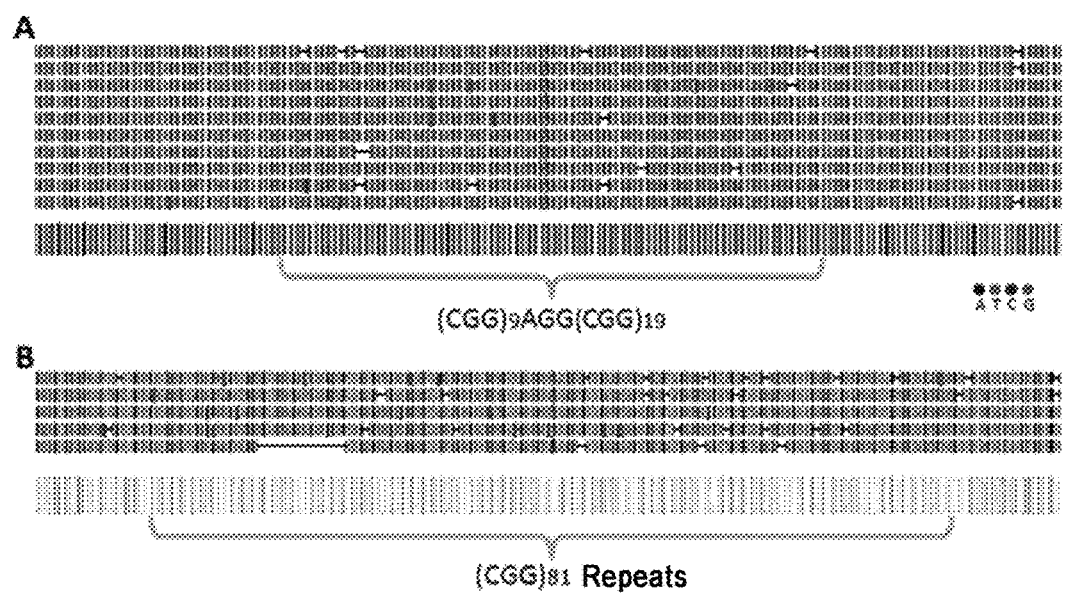

FIG. 4 shows the sequencing results of the enriched 5' un-translated region (5'UTR) with high GC content of the FMR1 gene from a normal sample (5'UTR of the FMR1 gene comprises 28 CGG repeats and 1 AGG, FIG. 4A) and a pro-mutant sample (5'UTR of the FMR1 gene comprises 81 CGG repeats, FIG. 4B) according to the method of the present application. The sequencing is performed on the PacBio platform.

Figure 5:
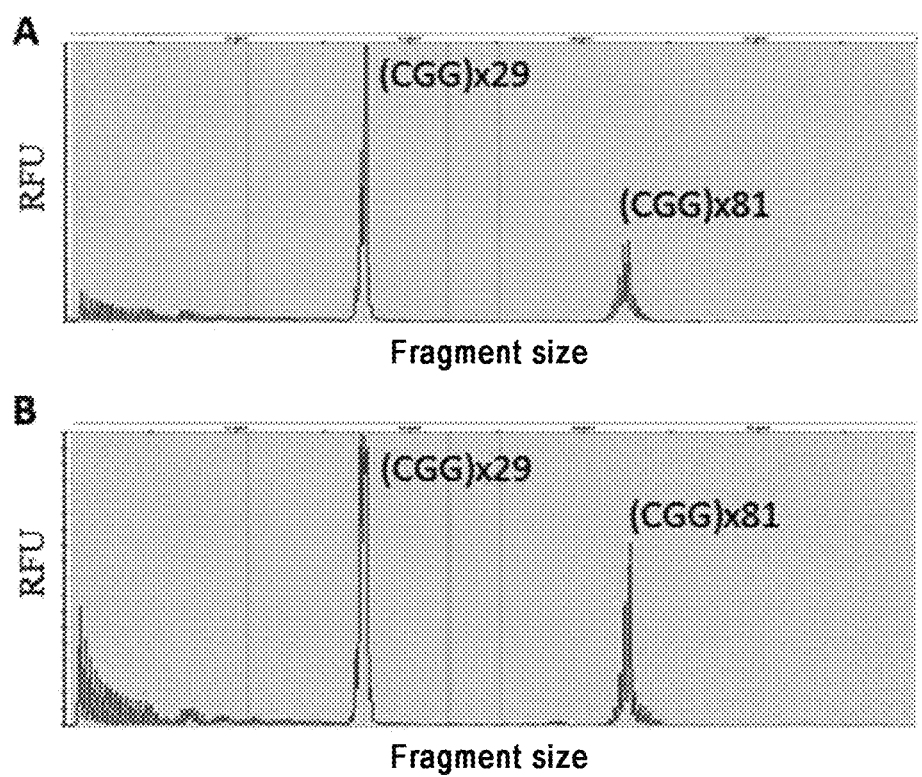

FIG. 5 shows the detection results of capillary electrophoresis performed on the target region of the genome DNA (FIG. 5A) and DNA enriched according to the present invention (FIG. 5B) using AmplideX® PCR/CE FMR1 Kit (Asuragen). Both the genome DNA and enriched DNA are derived from a hybrid sample, in which the 5'UTR of the FMR1 gene carry both 29 CGG repeats and 81 CGG repeats.

EXAMPLES

The present invention will be illustrated in more detail with reference to the figures and the following examples. It will be understand that the figures and examples of the present invention are only for illustration, and will not limit the scope of the present invention in any manner.

Example 1

This example shows the specific steps for enrichment of target DNA with high GC content followed by sequencing according to the method of the present invention.

It is known in the art that over 95% of the fragile X syndrome is caused by the abnormal number of (CGG)n tandem repeats in the 5'UTR region of the FMR1 gene. A healthy person generally has 6-40 repeats of CGG units, while patients with fragile X syndrome have significantly increased number of repeats, which can up to hundreds of, even thousands of repeats.

Samples used in this example are: (1) a normal sample, which comprises 28 CGG repeats and 1 AGG in 5'UTR of the FMR1 gene; and (2) a pro-mutant sample, which comprises 81 CGG repeats in 5'UTR of the FMR1 gene.

High GC regions of the 5'UTR of the FMR1 gene were enriched from the genome DNA of the normal sample and the pro-mutant sample using the method of the present invention according to the following protocol. The enriched regions were used for library construction, followed by the third generation sequencing performed on the PacBio platform.

Step 1: Capture of the Target DNA with High GC Content (1) Single-stranded oligonucleotide probes were designed against the specific flanking sequences of the high GC regions of the 5'UTR of the FMR1 gene (IDT Company). The SeqCap® EZ Hybridization and Wash Kit (NimbleGen) were used in the following operations.

Genome DNA was extracted, and 1.5 μg of genome DNA was mixed thoroughly in the system as indicated in the following table.

| Genome DNA | 1.5 μg |
|---|---|
| Human Cot-1 DNA (Invitrogen) | 5 μg |

The Human Cot-1 DNA was used to reduce non-specific hybridization. After mixing, the mixture was condensed to dry powder at 60° C. using a DNA condenser.

(2) The following reagents were added to the dry powder obtained in the previous step:

| NimbleGen 2× hybridization buffer | 10 μl |
|---|---|
| NimbleGen hybridization component A | 4 μl |

After dissolution and mixing, the mixture was reacted for 10 min at 95° C. Then, 6 μl (3 pmole) single-stranded oligonucleotide probes were added 30 s before the end of the reaction, while the reaction tube was maintained on the PCR machine. The mixture was mixed thoroughly, and hybridized for 16-20 h at 47° C.

(3) Cleaned Streptavidin Dynabeads® M270 (Thermo Fisher) were added into the hybridization system, and reacted 45 min for 47° C. The whole system was mixed thoroughly every 15 min, followed by sequential wash with washing buffers in the SeqCap® EZ Hybridization and Wash Kit. Then, 50 μl DNase-free and RNase-free water was added.

(1) 50 μl Dynabeads® obtained from step 1 was divided into 2 tubes. Amplification was carried out according to the following reaction 1 and reaction 2.

Reaction 1: a reaction mixture was prepared using 25 μl Dynabeads® as indicated in the following table, then reacted for 3 min at 95° C., and then for 15 min at 4° C. Random primers (100 μM) used was Exo-Resistant random primers from Thermo scientific.

| | |
|---|---|
| ddH$_2$O | 49 μl |
| Phi29 buffer (10X) | 10 μl |
| Random primers (100 μM) | 5 μl |
| Dynabeads | 25 μl |
| Total volume | 89 μl |

Reaction 2: when reaction 1 was finished, the obtained 89 μl product was prepared into reaction mixture as indicated in the following table, reacted for 18-20 h at 30° C., and then for 10 min at 65° C.

| | |
|---|---|
| Product from Reaction 1 | 89 μl |
| dNTP (10 mM) | 5 μl |
| 20 mg/ml BSA | 1 μl |
| Phi29 DNA polymerase | 5 μl |
| Total Volume | 100 μl |

At the end of reaction 2, the reaction mixture was transferred to a 1.5 ml centrifuge tube, and added with 0.4× AMPURE® XP beads, which was balanced for at least 30 min at room temperature in advance. The mixture was mixed and kept at room temperature for 15 min, followed by washing with 200μl 80% ethanol for twice and dried at room temperature. Then, 30μl EB buffer was added and eluted for 10 min. The whole system was then kept on a magnetic frame for 5 min, and supernatant was collected.

Step 3: Removal of Branched DNA Intermediate by Enzyme Digestion

A reaction system was prepared as indicated in the following table, and then reaction for 30 min at 37° C.

| | |
|---|---|
| Supernatant from step 2 | ≤1 μg |
| 10× Buffer 2 | 5 μl |
| T7 Endo I | 1 μl |
| ddH$_2$O added to total volume | 50 μl |

Step 4: Enriched Target DNA with High GC Content Obtained by Purification

The product obtained in step 3 was transferred to 1.5 ml concentration tube, while 20-30 ng was taken as control before purification. The remaining product was added into 0.4×AMPURE® XP beads, which was balanced for at least 30 min at room temperature in advance, mixed thoroughly and kept at room temperature for 15 min. After wash twice with 200μl of 80% ethanol, the mixture was dried at room temperature, added with 30 μl of EB buffer to elute for 10 min. The whole system was then kept on a magnetic frame for 5 min, and supernatant obtained was purified enriched target DNA with high GC content.

Figure 1:
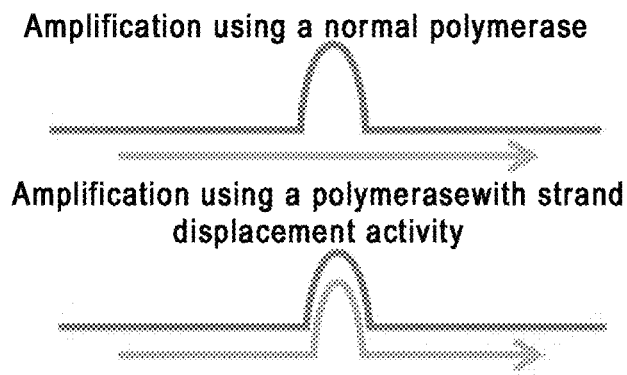
FIG. 1 shows that the DNA polymerase used in the multiple displacement amplification (MDA) can open the secondary structure of DNA, thus ensuring the accurate amplification of the high GC regions.
Figure 2:
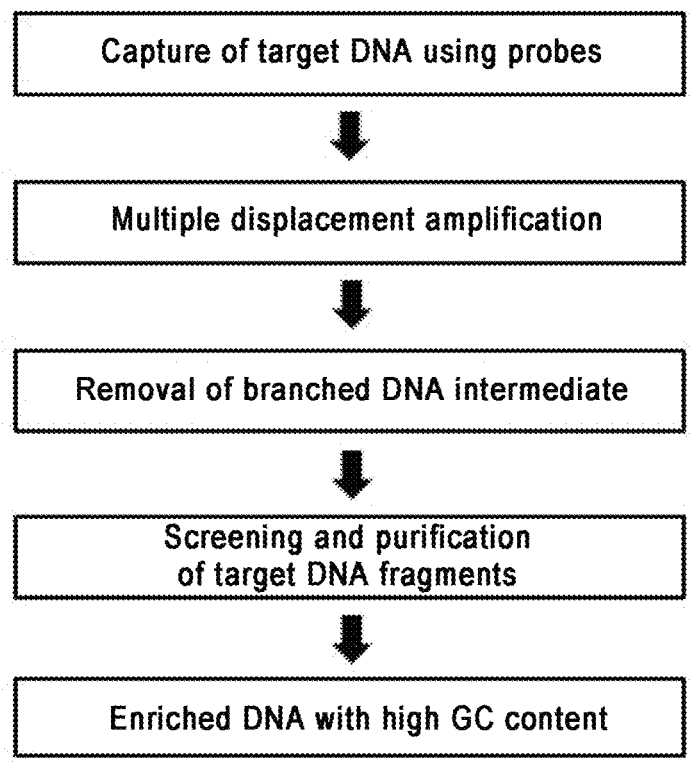
FIG. 2 is a scheme illustrating the method for enrichment of target DNA with high GC content according to the present invention.
Figure 3:
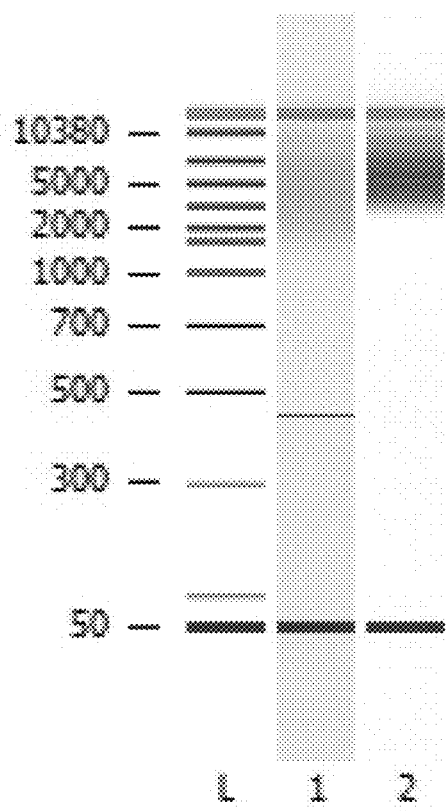
FIG. 3 shows that the sequencing library fragments obtained in examples of the present invention have a length over 2 kb. L: DNA ladder; 1: control before purification; 2: products after purification.

20-30 ng was taken as product after purification. The size of DNA fragments of control before purification and product after purification were detected by Agilent 2100 Bioanalyzer. The results are indicated in FIG. 3. Compared to the control before purification, the product after purification has a length greater than 2 kb, while the length distribution is more focused with a higher concentration.

Step 5: Third Generation Sequencing of the Target DNA with High GC Content

The product obtained in step 4 was connected with sequencing linkers to construct a library, which was then subjected to the third generation sequencing on the PacBio platform. The sequencing results are shown in FIG. 4. Both the high GC region comprising 28 CGG repeats and 1 AGG in the 5'UTR of FMR1 gene from the normal sample (FIG. 4A) as well as that comprising 81 CGG repeats in the 5'UTR of FMR1 gene from the pro-mutant sample (FIG. 4B) are sequenced with high accuracy, even the presence of 1 AGG in the normal sample is detected accurately. This result shows that the method according to the present invention can completely and accurately enrich target DNA with high GC content, thereby allowing the followed accurate sequencing.

Example 2

This example is to demonstrate the effects of the method according to the present invention in the enrichment of target DNA with high GC content.

The sample used in this example is a hybrid sample comprising FMR1 pro-mutant, that is, 5'UTR of the FMR1 gene carries both 29 CGG repeats and 81 CGG repeats. Two types of DNA were obtained from this sample: (1) the original genome DNA, and (2) target DNA comprising CGG repeats within 5'UTR of the FMR1 gene enriched from the genome DNA according to the method of the present invention. These two types of DNA were analyzed using AmplideX® PCR/CE FMR1 Kit (Asuragen, Patent Application No. CN201080032511) respectively for the CGG repeat regions in 5'UTR of the FMR1 gene, and the results obtained by high resolution capillary electrophoresis are shown in FIG. 5. It is clear that the CGG repeat region in 5'UTR of the FMR1 gene enriched according to the method of the present invention (FIG. 5B) has the same number of CGG repeats as the CGG repeat region in 5'UTR of the FMR1 gene from the original genome DNA. This result shows that the method according to the present invention can completely and accurately enrich target DNA with high GC content.

It will be understand that the features of the present invention illustrated by the above examples are not intended to limit the scope of the present application. Various modification and changes are within the knowledge of one skilled in the art. The reaction reagents, reaction conditions and the like involved in sequencing library construction can be adjusted and varied accordingly as needed. Without departing the concept and principle of the present invention, various simple substitutions can be made within the knowledge of one skilled in the art, which are still encompassed in the scope of the present invention.

REFERENCES

[1] Jia Q, Wu H, Zhou X, et al. A "GC-rich" method for mammalian gene expression: a dominant role of non-coding DNA GC content in regulation of mammalian gene expression. *Sci China Life Sci* 2010, 53(1): 94-100.

[2] Huang W, Xia Q, Luo S, et al. Distribution of fragile X mental retardation 1 CGG repeat and flanking haplotypes in a large Chinese population. *Mol Genet Genomic Med.* 2015, 3(3):172-181.

[3] Chen X, Wang J, Xie H, et al. Fragile X syndrome screening in Chinese children with unknown intellectual developmental disorder. *BMC Pediatr.* 2015, 15: 77.
[4] Kieleczawa J. Fundamentals of sequencing of difficult templates—an overview. *J Biomol Tech.* 2006, 17(3):207-217.
[5] Hubé F, Reverdiau P, lochmann S, Gruel Y. Improved PCR method for amplification of GC-rich DNA sequences. *Mol Biotechnol* 2005, 31(1):81-84.
[6] Li L Y, Li Q, Yu Y H, et al. A primer design strategy for PCR amplification of GC-rich DNA sequences. *Clin Biochem.* 2011, 44(8-9):692-698.
[7] Jensen M A, Fukushima M, Davis R W. DMSO and betaine greatly improve amplification of GC-rich constructs in de novo synthesis. *PLoS One.* 2010, 5(6): e11024.
[8] Strien J, Sanft J, Mall G. Enhancement of PCR amplification of moderate GC-containing and highly GC-rich DNA sequences. *Mol Biotechnol.* 2013, 54(3):1048-1054.
[9] Loomis E W, Eid J S, Peluso P, et al. Sequencing the unsequenceable: expanded CGG-repeat alleles of the fragile X gene. *Genome Res.* 2013, 23(1):121-128.
[10] Schadt E E, Turner S, Kasarskis A. A window into third-generation sequencing. *Hum. Mot Genet.* 2010, 19(R2): R227-R240.
[11] Pham T T, Yin J, Eid J S, et at Single-locus enrichment without amplification for sequencing and direct detection of epigenetic modifications. *Mol Genet Genomics.* 2016, 291(3):1491-1504.
[12] Horn S. Target Enrichment via DNA Hybridization Capture. In: Shapiro B., Hofreiter M. (eds) Ancient DNA. *Methods in Molecular Biology (Methods and Protocols)*, 2012, vol 840. Humana Press.
[13] Dean F B, Hosono S, Fang L, et al. Comprehensive human genome amplification using multiple displacement amplification. *Proc Natl Acad Sci USA.* 2002, 99(8):5261-5266.

What is claimed is:

1. A method for enrichment of target DNA with high GC content, comprising the following steps:
    (a) designing single-stranded oligonucleotide probes against specific flanking sequences of the target DNA with high GC content, and capturing the target DNA from genome DNA by target sequence capture technology;
    (b) amplifying the captured target DNA with high GC content using multiple displacement amplification so as to obtain an amplification product;
    (c) subjecting the amplification product to enzyme digestion to remove branched DNA intermediates, so as to obtain a digested product;
    (d) purifying a DNA fragment with a length equal to or larger than 2 kb in the digested product, so as to obtain enriched target DNA with high GC content.

2. The method according to claim 1, characterized in that, the GC content of the target DNA with high GC content is between 80% and 100%.

3. The method according to claim 1, characterized in that, said target sequence capture technology is hybridization between the single-stranded oligonucleotide probes and genome DNA.

4. The method according to claim 1, characterized in that, the captured target DNA has a length of 2 kb to 30 kb.

5. The method according to claim 1, characterized in that, the single-stranded oligonucleotide probes carry a biotin label.

6. The method according to claim 1, characterized in that, the multiple displacement amplification uses a polymerase for isothermal amplification with strand displacement activity.

7. The method according to claim 1, characterized in that, the multiple displacement amplification uses primers modified with 3'-thiophosphate bonds.

8. The method according to claim 1, characterized in that, the enzyme digestion is performed using a nuclease.

9. A kit for enrichment of target DNA with high GC content, comprising
    single-stranded oligonucleotide probes against specific flanking sequences of the target DNA with high GC content, wherein the single-stranded oligonucleotide probes carry a biotin label,
    reagents for multiple displacement amplification,
    reagents for removing branched DNA intermediates by enzyme digestion, and
    reagents for purifying DNA fragments with a length equal to or larger than 2 kb.

10. The kit according to claim 9, characterized in that, the GC content of the target DNA with high GC content is between 80% and 100%.

11. The kit according to claim 9, characterized in that, the reagents for multiple displacement amplification comprise a polymerase for isothermal amplification and primers.

12. The kit according to claim 9, characterized in that, the reagents for removing branched DNA intermediates comprise a nuclease.

13. A method for constructing a sequencing library of target DNA with high GC content, comprising the following steps:
    (1) enriching target DNA with high GC content using the method according to any one of claims 1-8;
    (2) ligating enriched target DNA with high GC content to sequencing linkers, so as to obtain the sequencing library.

14. The method according to claim 13, wherein the sequencing library is suitable for long reads high-throughput sequencing platforms.

* * * * *